US00PP31835P2

(12) United States Plant Patent
Zary

(10) Patent No.: US PP31,835 P2
(45) Date of Patent: Jun. 2, 2020

(54) CRAPE MYRTLE PLANT NAMED 'GARZARNOBEFU'

(50) Latin Name: *Lagerstroemia indica*
Varietal Denomination: GARzarnobefu

(71) Applicant: Early Morning LLC, Greendale, IN (US)

(72) Inventor: Keith W. Zary, Missoula, MT (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/602,342

(22) Filed: Sep. 17, 2019

(51) Int. Cl.
*A01H 5/00* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new and distinct variety of crape myrtle plant having an upright, well-branched and compact shrub numerous flowers on panicles and resistance to leaf spot and powdery mildew strains found in Ohio and California, is disclosed.

2 Drawing Sheets

Genus and species: *Lagerstroemia indica.*
Denomination: 'GARzarnobefu'.

BACKGROUND

'GARzarnobefu' is a new and distinct variety of crape myrtle. 'GARzarnobefu' originated from a controlled cross in August 2011 in Tipp City, Ohio between the female parent, an unnamed and unpatented seedling derived from the cross between the crape myrtle plants 'Baton Rouge' (unpatented) and 'Dynamite' (U.S. Plant Pat. No. 10,269) and the male parent, an unnamed and unpatented crape myrtle seedling.

The resulting seeds from the cross were collected in August 2011 and planted and evaluated in Tipp City, Ohio. 'GARzarnobefu' was selected in July 2012 from the population of seedlings in Tipp City, Ohio. 'GARzarnobefu' was first asexually propagated in July 2013 in Tipp City, Ohio from softwood cuttings.

Other subsequent asexual propagations were conducted in controlled environments in Tipp City, Ohio and demonstrate that 'GARzarnobefu' reproduces true to type in successive generations of asexual reproduction via softwood cuttings.

SUMMARY

The following are the most outstanding and distinguishing characteristics of this new variety when grown under normal horticultural practices in Tipp City, Ohio.

1. An upright, well-branched and compact shrub having numerous flowers on panicles; and
2. Resistance to leaf spot and powdery mildew strains found in Ohio and California.

DESCRIPTION OF THE PHOTOGRAPHS

This new crape myrtle plant is illustrated by the accompanying photographs which show the plant's overall plant habit including form, foliage, and flowers. The photographs are of a 4-year old plant grown outdoors in Tipp City, Ohio in August 2019. The colors shown are as true as can be reasonably obtained by conventional photographic procedures.

DETAILED DESCRIPTION

Figure 1:
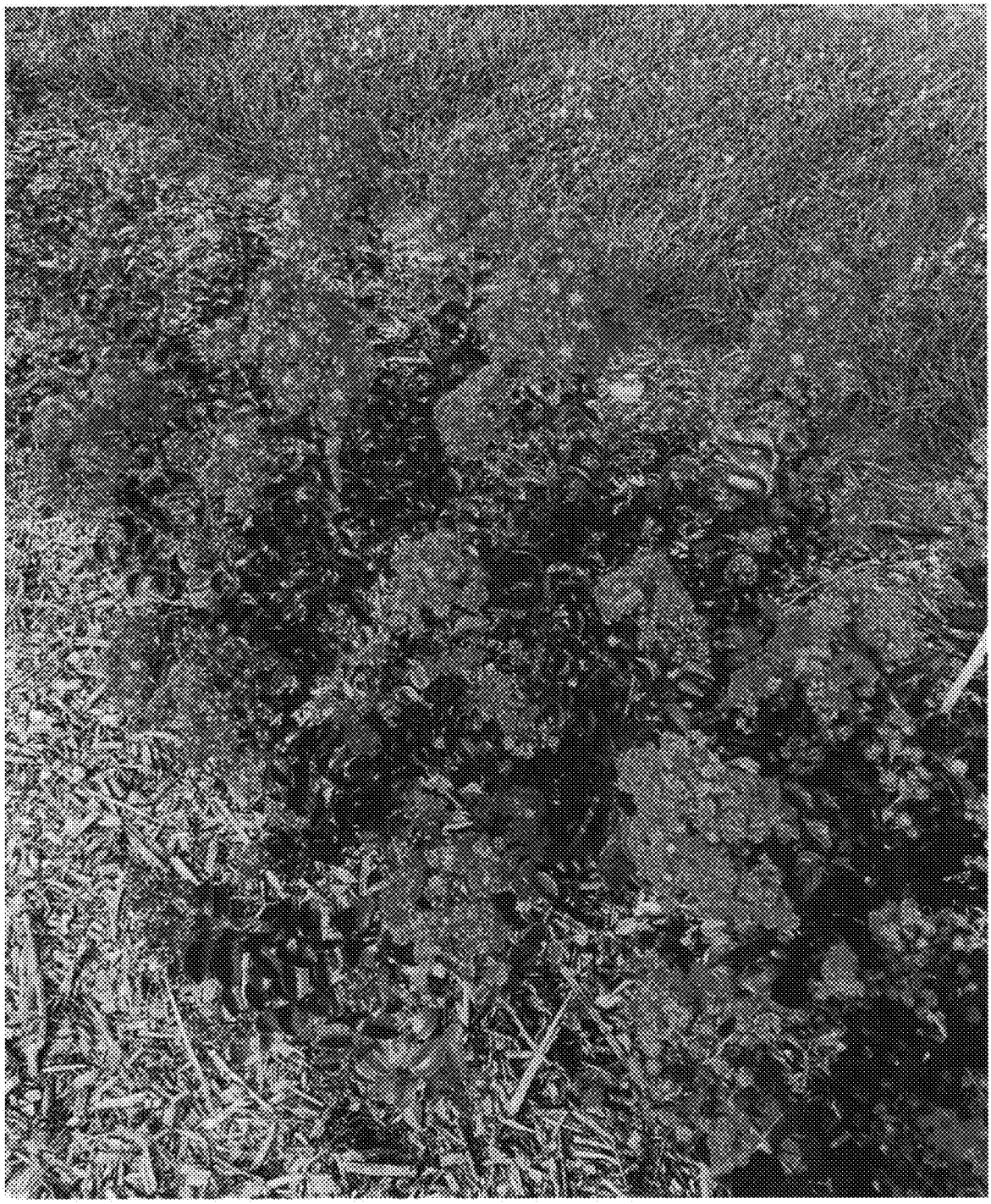
FIG. 1 shows the overall plant habit of 'GARzarnobefu'.
Figure 2:
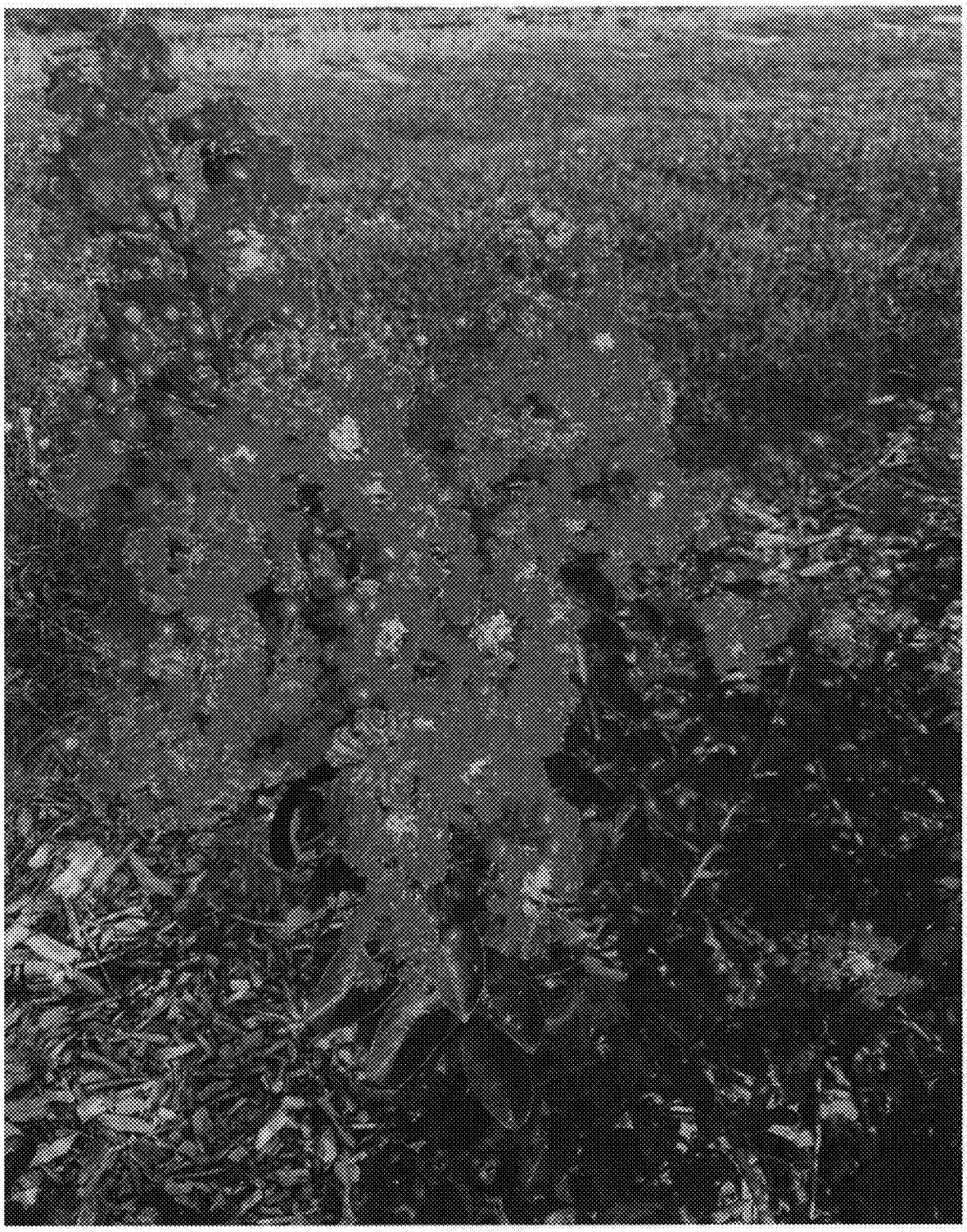
FIG. 2 shows a close-up of the individual flowers, buds, foliage, and bark of the plant.

The following detailed descriptions set for the distinctive characteristics of 'GARzarnobefu'. The data which define these characteristics were collected outdoors in Tipp City, Ohio. Plants were planted in spring 2015 from cuttings taken in 2014 and evaluated in an outdoor field in Tipp City, Ohio in August 2019. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
*Family.*—Lythraceae.
*Species.*—*Lagerstroemia indica.*
*Variety.*—'GARzarnobefu'.

Parentage:
*Female parent.*—An unnamed and unpatented seedling derived from a cross between the crape myrtle plants 'Baton Rouge' (unpatented) and 'Dynamite' (U.S. Plant Pat. No. 10,269).
*Male parent.*—An unnamed and unpatented crape myrtle seedling.

Propagation:
*Type.*—Softwood cuttings.
*Time to initiate roots.*—Three weeks.
*Time to produce a rooted young plant.*—8 to 10 weeks.

*Root description.*—Fine and fibrous; RHS 177C.
*Rooting habit.*—Fibrous and well-branched.

Plant description:
*Plant form and growth habit.*—Upright and compact.
*Branching habit.*—Well-branched.
*Plant height.*—80.0 cm to 90.0 cm.
*Plant diameter* (*area of spread*).—60.0 cm to 70.0 cm.

Lateral branch description:
*Length.*—45.0 cm to 50.0 cm.
*Diameter.*—10.0 mm to 11.0 mm.
*Internode length.*—2.2 cm.
*Strength.*—Strong.
*Texture, immature.*—Smooth and stems are terete; four longitudinal carinae on either side of the petioles.
*Texture, mature.*—Rough with some exfoliation; stems are terete; four longitudinal carinae on either side of the petioles.
*Color, immature.*—RHS 183B to RHS 183C.
*Color, mature.*—RHS N165A.

Bark:
*Immature stem color.*—RHS 183B to RHS 183C.
*Mature stem color.*—RHS N165A.

Leaf:
*Arrangement.*—Sub-opposite to alternate.
*Length.*—5.1 cm.
*Width.*—3.5 cm.
*Shape.*—Oval.
*Apex.*—Rounded to attenuate.
*Base.*—Ciliolate.
*Margin.*—Entire, ciliolate.
*Texture.*—Upper surface: Lustrous, leathery. Lower surface: Lustrous.
*Venation pattern.*—Pinnate.
*Venation color.*—Upper surface: RHS 147C. Lower surface: RHS 147D with blush of RHS 181D at the base.
*Immature leaf color.*—Upper surface: RHS 166A. Lower surface: RHS 175A.
*Mature leaf color.*—Upper surface: RHS 139A. Lower surface: RHS 147B.
*Petioles.*—Length: 1.0 mm. Color: RHS 147B blushed with RHS 181D. Texture: Smooth.

Flower:
*Flower arrangement and flowering habit.*—Panicle averaging about 70 to 80 flowers of main shoots followed by lateral shoots.
*Natural flowering season.*—Late July through August in Southwest Ohio (about 6 to 7 weeks); a second flush of flowering occurs in longer growing seasons like California.
*Fragrance.*—None.
*Inflorescence height.*—45.0 cm.
*Inflorescence diameter.*—30.0 cm.
*Flower diameter.*—3.7 cm.
*Flower length.*—2.0 cm.
*Flower buds.*—Globose; smooth/glabrous; slightly cuspidate apex and rounded base; 8.0 mm length and 6.0 mm wide.
*Flower bud color.*—RHS 45A to RHS 45B.

Petals:
*Quantity.*—6 per flower.
*Lobe length.*—1.1 cm.
*Lobe width.*—1.0 cm.
*Lobe shape.*—Ruffled or crisped.
*Apex.*—Rounded and ruffled.
*Base.*—Adnate to calyx.
*Margin.*—Crisped.
*Texture* (*both upper and lower surfaces*).—Thin, soft.
*Color* (*both upper and lower surfaces*).—RHS N78A.

Sepals:
*Quantity and arrangement.*—6 and fused at the base.
*Length.*—Above the fused portion, the length is 3.5 mm.
*Width.*—Above the fused portion, the width is 4.0 mm.
*Shape.*—Triangular.
*Apex.*—Acute.
*Base.*—Fused.
*Margin.*—Entire.
*Color.*—Upper surface: RHS 178B. Lower surface: RHS 145D except on tips where exposed to light as flower opens, which is blushed with RHS 178D.

Peduncles:
*Length.*—Up to 45.0 cm.
*Diameter.*—5.0 mm.
*Strength.*—Strong.
*Texture.*—Base has some exfoliation.
*Color.*—Base color is near RHS 165A, while terminal color is RHS 183B to RHS 183C.

Pedicels:
*Length.*—5.0 mm.
*Diameter.*—1.0 mm.
*Strength.*—Strong.
*Texture.*—Smooth.
*Color.*—RHS 187B to RHS 187C.

Reproductive organs:
*Androecium.*—Quantity of stamens per flower: About 40; 6 long stamens and about 34 shorter stamens. Filament length: 12.0 mm for the longer stamens and 4.0 mm for the shorter stamens. Anther shape: Flattened ellipsoid. Anther length: 1.5 mm on the longer stamens and 1.0 mm on the shorter stamens. Anther color: RHS 14D. Amount of pollen: Abundant. Pollen color: RHS 22A.
*Gynoecium.*—Quantity of pistils per flower: 1. Pistil Length: 16.0 mm. Style length: 16.0 mm. Style color: RHS 183C. Stigma color: RHS 183A. Stigma shape: Globose. Ovary color: RHS 157B.

Fruit and seed set: Seed is present; it is globose in shape, a 6-valved dehiscent capsule that is about 6.0 mm wide and 8.0 mm in length; apex and base are rounded color is RHS 165A.

Disease and insect resistance: Resistant to powdery mildew strains *Erysiph* found in Ohio and California and resistant to leaf spot, *Cercospora*.

COMPARISON WITH PARENTAL AND COMMERCIAL LINES

Table 1 shows a comparison of differences between 'GARzarnobefu' and both parental lines.

TABLE 1

| Comparison with Parental Lines | | | |
|---|---|---|---|
| Characteristic | 'GARzarnobefu' | Female parent, un-named crape myrtle seedling | Male parent, unnamed crape myrtle seedling |
| Flower color | RHS N78A | RHS 53C | RHS 55D |
| Plant habit and size | Upright and 80 cm to 90 cm by 70 cm | Upright and 120 cm by 110 cm | Upright and 60 cm by 40 cm |

Table 2 shows a comparison of the differences between 'GARzarnobefu' and the commercial crape myrtle variety 'Macchiato' (U.S. Plant Pat. No. 28,759).

TABLE 2

| Comparison with Commercial Line | | |
|---|---|---|
| Characteristic | 'GARzarnobefu' | 'Macchiato' |
| Flower color | RHS N78A | RHS 71A to RHS 71B |
| Plant habit and size | Upright and 90 cm by 70 cm | Rounded and 45 cm by 43 cm |

I claim:

1. A new and distinct variety of crape myrtle plant designated 'GARzarnobefu' as illustrated and described herein.

* * * * *